(12) United States Patent
Heinz et al.

(10) Patent No.: US 10,292,794 B2
(45) Date of Patent: May 21, 2019

(54) METHOD AND SYSTEM FOR THE CONSTRUCTION OF A DENTAL PROSTHESIS

(71) Applicant: Ivoclar Vivadent AG, Schaan (LI)

(72) Inventors: Markus Heinz, Naturns (IT); Hans Peter Foser, Balzers (LI); Wolfgang Ruess, Schellenberg (LI); Thomas Baaske, Grabs (CH)

(73) Assignee: Ivoclar Vivadent AG, Schaan (LI)

( * ) Notice: Subject to any disclaimer, the term of this patent is extended or adjusted under 35 U.S.C. 154(b) by 119 days.

(21) Appl. No.: 14/652,622

(22) PCT Filed: Nov. 26, 2013

(86) PCT No.: PCT/EP2013/074768
§ 371 (c)(1),
(2) Date: Jun. 16, 2015

(87) PCT Pub. No.: WO2014/095269
PCT Pub. Date: Jun. 26, 2014

(65) Prior Publication Data
US 2016/0193019 A1 Jul. 7, 2016

(30) Foreign Application Priority Data
Dec. 17, 2012 (EP) ..................................... 12197441

(51) Int. Cl.
*A61C 13/007* (2006.01)
*A61C 13/08* (2006.01)
(Continued)

(52) U.S. Cl.
CPC ............ *A61C 13/081* (2013.01); *A61C 13/00* (2013.01); *A61C 13/0004* (2013.01); *A61C 13/0006* (2013.01); *A61C 13/01* (2013.01); *A61C 13/097* (2013.01); *A61C 13/1006* (2013.01); *A61C 13/1016* (2013.01); *A61C 19/045* (2013.01);
(Continued)

(58) Field of Classification Search
CPC ... A61C 13/00; A61C 13/0004–13/006; A61C 13/01–13/081; A61C 5/70; A61C 5/77; A61C 19/045; A61C 19/05
See application file for complete search history.

(56) References Cited

U.S. PATENT DOCUMENTS 4,345,900 A 8/1982 Katz et al.
2010/0332253 A1* 12/2010 Adusimilli ............. A61C 11/00
705/2

(Continued)

OTHER PUBLICATIONS

International Preliminary Report on Patentability of PCT/EP2013/074768, dated Jul. 2, 2015, 8 pages.
(Continued)

*Primary Examiner* — Tammie K Marlen
(74) *Attorney, Agent, or Firm* — Ann M. Knab; Thad McMurray (57) ABSTRACT

Method and system for the construction of a total dental prosthesis, wherein the shapes of the upper and lower jaw bases taken in the plastic material are digitized and stored as a digital prosthesis model in a data-processing device, and the upper and lower jaw prosthesis bases are produced from dental materials according to the digital prosthesis model by ablative or constructive methods.

13 Claims, 10 Drawing Sheets

(51) Int. Cl.
  *A61C 19/05*   (2006.01)
  *A61C 13/00*   (2006.01)
  *A61C 13/01*   (2006.01)
  *A61C 19/045*  (2006.01)
  *A61C 13/36*   (2006.01)
  *A61C 13/097*  (2006.01)
  *A61C 13/093*  (2006.01)

(52) U.S. Cl.
  CPC ......... *A61C 19/05* (2013.01); *Y10T 29/49567* (2015.01)

(56) References Cited

U.S. PATENT DOCUMENTS

| | | |
|---|---|---|
| 2015/0132718 A1* | 5/2015 | Kerschensteiner ........................ A61C 13/0004 433/196 |
| 2015/0134094 A1 | 5/2015 | Thompson et al. |
| 2016/0008108 A1 | 1/2016 | Thompson et al. |

OTHER PUBLICATIONS

Becker, W., CAD and CAM—Great Potential for Full Dentures (I), Quintessenz Zahntech 17, 397-404, Apr. 1991.
Becker, W., CAD and CAM—Great Potential for Full Dentures (II), Quintessenz Zahntech 17, 511-519, May 1991.

\* cited by examiner

METHOD AND SYSTEM FOR THE CONSTRUCTION OF A DENTAL PROSTHESIS

CROSS-REFERENCE TO RELATED APPLICATIONS

This application is a National Stage application of International patent application PCT/EP2013/074768 filed on Nov. 26, 2013, which claims priority to European patent application No. 12197441.4 filed on Dec. 17, 2012, the disclosures of which are incorporated herein by reference in their entirety.

The invention relates to a method for the construction of a dental prosthesis, wherein the shapes of upper and lower jaw bases are taken with plastic material using standard impression trays or individualized impression trays, which have been produced in a manner individually adapted to the patient's jaw on the basis of prior acquisition of the shapes using standard impression trays or by acquiring the shapes by digital scanning and/or phototechnical acquisition, when taking the shapes of the upper and lower jaw bases, the position of the occlusal plane relative to the upper and lower jaw bases is acquired with a bite fork by alignment parallel to the bipupillar line and the Camper plane and is digitally stored, the shapes of the upper and lower jaw bases taken in the plastic material are digitized and stored as a digital prosthesis model in a data-processing device, the upper and lower jaw prosthesis bases are produced from dental materials according to the digital prosthesis model by ablative or constructive methods.

The invention furthermore relates to a system for the construction of a total dental prosthesis, having standard impression trays or individualized impression trays for taking the shapes of upper and lower jaw bases with plastic material, the individualized impression trays having been produced in a manner individually adapted to the patient's jaw on the basis of prior acquisition of the shapes using standard impression trays or by acquiring the shapes by digital scanning and/or phototechnical acquisition, a bite fork for acquiring the position of the occlusal plane by alignment parallel to the bipupillar line and the Camper plane when taking the shapes of the upper and lower jaw bases, and a memory for storing the digitized position of the occlusal plane relative to the upper and lower jaw bases, a sampling device for acquiring and digitizing the shapes of the upper and lower jaw bases taken in the plastic material, a data-processing device for storing the digitized shapes of the upper and lower jaw bases as a digital prosthesis model, a manufacturing apparatus for producing the upper and lower jaw prosthesis bases from dental materials according to the digital prosthesis model by ablative or constructive methods under the control of the data-processing device.

An early method and system in this direction is known, for example, from the article "CAD and CAM—Möglichkeiten der Optimierung in der Totalprothetik" [CAD and CAM—possibilities of optimization in total prosthetics], Wolfgang Becker, which was published in two parts in Quintessenz Zahntechnik 17, 397-404 (1991) and 511-519 (1991). It is proposed therein to acquire the shapes of the upper and lower jaw bases phototechnically, and to generate a digital model of the upper and lower jaw bases therefrom. These data are used in a subsequent computer-controlled milling process in order to produce the upper and lower jaw prosthesis bases.

A method according to the precharacterizing clause of Patent Claim 1 is known from WO 2012/061652 A2. In the known method, the shapes of the upper and lower jaw bases are taken as impressions in the plastic material with standard impression trays or with individualized impression trays. Here, the term individualized impression trays refers to ones which have been obtained on the basis of prior acquisition of the shapes of the upper jaw and lower jaw, and which are thus already individually adapted to the specific anatomy of the patient. During, before or after the impression, various anatomical data of the patient may be recorded, and for example the position of the occlusal plane relative to the upper and lower jaw bases may be determined and stored. In a system actually proposed by the Applicant, templates of a front dental arch are also used, the position of which with respect to the impression trays is marked by application onto the impression tray. The position of the front dental arch template is also digitized during the digital sampling of the upper and lower jaw bases taken in the plastic material, and is thus included in the digital prosthesis model.

A very similar computer implemented method is known from WO 2012/061655 A2 which method, besides the above described steps, designs or selects teeth by applying a number of predetermined rules, which teeth are best matching to a particular jaw base. The teeth may for example be selected from a library including a plurality of stored teeth.

It is an object of the present invention to provide an improved method and an improved system for the construction of a dental prosthesis, in which a digital prosthesis model with improved positioning of the tooth installation can be generated. A more expedient selection of an optimal front dental arch for the prosthesis is furthermore intended to be made possible.

This object is achieved by the method having the features of Patent Claim 1 and by the system having the features of Patent Claim 11. Advantageous embodiments are specified in the dependent claims.

In the method according to the invention, a set of upper or lower standard front dental arches is provided, the set containing standard front dental arches with different front tooth sizes and front tooth shapes. For each front dental arch in the set of standard front dental arches provided, their shape data which represent a three-dimensional spatial description of the teeth of the front dental arch are stored in a database. When taking the shapes of the upper and lower jaw bases with plastic material in the impression trays, a front dental arch which best matches the situation in the patient's jaw is selected from the set of standard front dental arches provided. This selected standard front dental arch is then positioned on the impression tray, so that it obtains the desired position in the jaw, and is fastened in this position on the impression tray. In order to form a starting point for the digital prosthesis model, the shapes of the upper and lower jaw bases taken in the plastic material in the impression trays with the front dental arch fastened on one of the impression trays are digitized by scanning in a registered bite position and are stored. From the database with the front dental arch shape data of the set of standard front dental arches, the front dental arch shape data which belong to the selected standard front dental arch are then called up. These are then spatially positioned in the digital prosthesis model in such a way that there is the least possible deviation with respect to the position of the actually scanned selected front dental arch fastened on the impression tray. In other words, the position of the imported front dental arch shape data of the selected standard front dental arch in the digital spatial model of the prosthesis is varied by displacement and turning until a minimum deviation is achieved relative to the scanned front dental arch.

In this way, when impressing the shapes of the upper and lower jaw bases, it is possible for the dental technician or dental surgeon to try different ones from a provided set of standard front dental arches and select one which is most suitable.

This is then fastened in its desired position on the impression tray, so that its future position in the digital prosthesis model can be established. A higher accuracy of the digital prosthesis model is made possible by importing the standard front dental arch shape data of the selected standard front dental arch from the database.

The method may for example be carried out by a dental surgeon or dental technician, who carries out the impressions and produces the impression trays with the shapes of the upper and lower jaw bases taken in the plastic material and the front dental arch fastened thereon in a registered bite position. The impression trays with the shapes taken thereon and the front dental arches fastened thereon may then be taken to a dental laboratory where this shape is digitized by scanning and stored, in order to form a starting point for the digital prosthesis model. In the dental laboratory, the digital prosthesis model may then be automatically completed in the data-processing device by calling up shape data for standard front dental arches and premolar tooth rows, and also interactively gradually improved by the user by inputs and further shapings. The final digital prosthesis model obtained in this way may, for example, then be used in a CAM method for milling the prosthesis bases from plastic blocks.

In a preferred embodiment, the data-processing device may be adapted to call up an antagonist standard front dental arch matching the selected standard front dental arch for the upper or lower jaw in the form of digital antagonist standard front dental arch shape data from the database and position it with the data of the associated jaw base in the digital prosthesis model, in such a way that an optimal position with respect to the selected standard front dental arch is achieved, the shape data of which have already previously been integrated from the database into the digital prosthesis model.

In another preferred embodiment, after integration of the standard front tooth shape data and optionally antagonist standard front tooth shape data with the digitized data of the associated jaw base, one or more premolar tooth rows matching the front dental arch are automatically offered for selection by the data-processing device and, after selection by the user, digital premolar tooth row shape data describing these are called up from the database and subsequently entered with the digitized jaw base data into the digital prosthesis model in a manner matching the already integrated standard front dental arch shape data.

In a preferred embodiment, the data-processing device generates a graphical representation of the digital prosthesis model and shows it on a screen. The data-processing device provides program functions, with which the digital prosthesis model can be manipulated by acting on the graphical representation. In particular, a digital wax knife is provided as a program function, in order to configure the design of the gum and the prosthesis base surfaces with the digital wax knife in the graphical representation of the digital prosthesis model and to transfer the configurations carried out in this way into the digital prosthesis model.

In a preferred embodiment, the data-processing device provides a multiplicity of predetermined surface textures for selection, which can be applied after selection to desired regions of the surfaces of the digital prosthesis model.

In a preferred embodiment, at least one gingiva parameter is called up for specification by the data-processing device. This is at least one of the following gingiva parameters: gingival frame of the tooth lengths of the installed teeth (i.e. the depth to which the tooth base extends into the cavity in the prosthesis base), minimum wall thickness of upper and lower jaw bases (i.e. a minimum thickness which the prosthesis base must have at each point), surface texture parameters of the palate surface and geometrical parameters of the transition region from the prosthesis body to the tooth (i.e. the inner wall of the cavity need not merge with a sharp edge into the adjacent prosthesis base surface above, but rather the transition region may be rounded); these entered gingiva geometrical parameters are transferred into the digital prosthesis model.

In a preferred embodiment, at least one tooth cavity parameter is called up by the data-processing device for specification, to which the width of the adhesive gap between the inner wall of the tooth cavity and the inserted tooth base and the position and number of spacers on the inner wall of the tooth cavity, with which the tooth base is held while being positioned in a defined way in the tooth cavity, in order to ensure an adhesive gap with the desired width between the inner walls of the tooth cavity and the tooth base everywhere, belong; the specified tooth cavity parameters for all tooth cavities are transferred into the digital prosthesis model.

In a preferred embodiment, when, during the calculation of the cavities for prefabricated plastic teeth, it is established that the remaining wall thickness of the prosthesis base below the cavity would fall below a predetermined minimum wall thickness, the length to which the plastic tooth is to be reduced in order to obtain the predetermined minimum wall thickness below the cavity is calculated and stored in the data-processing device. The cavity is then stored in the digital prosthesis model having been adapted to the reduced length of the plastic tooth. Furthermore, the plastic tooth is shortened to the stored reduced length of the plastic tooth in a milling device under the control of the data-processing device.

In a preferred embodiment, the data-processing device provides a selection menu for artificial teeth made of different material types, in which a material selection from dental materials is possible for each tooth position. Possible dental materials are PMMA, composite, zirconium dioxide, lithium disilicate and dental ceramic. In the data-processing device, the selected material type is then stored in the digital prosthesis model.

In a preferred embodiment, a bite fork which has an inner bite arch and an outer arch applied thereon using articulations is used for determining the position of the occlusal plane. The inner arch is introduced between the standard impression trays or the individualized impression trays. Selectively, the bite fork may be fastened on the upper and/or lower impression tray by means of an interface. The outer arch is then adjusted parallel to the Camper plane and parallel to the bipupillar line by turning the articulations. The resulting deviations of the parallelism of the inner bite arch from the aligned outer arch are read from a scale on the articulations and stored.

The invention furthermore relates to a system for the construction of a total dental prosthesis, having standard impression trays or individualized impression trays for taking the shapes of upper and lower jaw bases with plastic material, the individualized impression trays having been produced in a manner individually adapted to the patient's jaw on the basis of prior acquisition of the shapes using standard impression trays or by acquiring the shapes by digital scanning and/or phototechnical acquisition, a bite fork for acquiring the position of the occlusal plane by alignment parallel to the bipupillar line and the Camper plane when taking the shapes of the upper and lower jaw bases, and a memory for storing the digitized position of the occlusal plane relative to the upper and lower jaw bases, a sampling device for acquiring and digitizing the shapes of the upper and lower jaw bases taken in the plastic material, a data-processing device for storing the digitized shapes of the upper and lower jaw bases as a digital prosthesis model, a manufacturing apparatus for producing the upper and lower jaw prosthesis bases from dental materials according to the digital prosthesis model by ablative or constructive methods under the control of the data-processing device, characterized in that a set of upper or lower standard front dental arches is provided for selection and means are provided for fastening a selected standard front dental arch in the desired position on the impression tray with the upper or lower jaw base impressed therein in the plastic material, in order to form a starting point for the digital prosthesis model, the sampling device is adapted to digitize and store the shapes of the upper and lower jaw bases taken in the plastic material in the impression trays with the front dental arch fastened on one of the impression trays in a registered bite position by scanning, the data-processing device is adapted to call up the standard front dental arch shape data describing the selected standard front dental arch from a database, which contains digital standard front dental arch shape data for all standard front dental arches, and to integrate them with the data of the associated jaw base in the digital prosthesis model, in such a way that the position of the digital standard front dental arch shape data relative to the digitized jaw base data corresponds as well as possible to the position of the standard front dental arch, fastened on the impression tray, relative to the impressed jaw base.

In a preferred embodiment of the system, the data-processing device is adapted, for the selected standard front dental arch for the upper or lower jaw, to call up a matching antagonist standard front dental arch from the database in the form of digital antagonist front dental arch shape data and introduce it into the digital model of the associated jaw base in the digital prosthesis model, in such a way that an optimal match with the selected standard front dental arch is achieved.

In a preferred embodiment of the system, the data-processing device is adapted, after integration of the standard front dental arch shape data and optionally antagonist standard front dental arch shape data into the digital prosthesis model, to offer one or more premolar tooth rows characterized so as to match the selected standard front dental arch for selection. After selection of the corresponding digital premolar tooth row shape data called up from the database, these are entered into the digital prosthesis model in a manner matching the already integrated standard front dental arch shape data.

In a preferred embodiment of the system, it comprises a graphical display and the data-processing device is adapted to show a graphical representation of the digital prosthesis model on the display. A digital wax knife is provided as a program function by the data-processing device, in order to allow a user to design the gum and the prosthesis base surfaces with the digital wax knife in the graphical representation of the digital prosthesis model. The configurations of the gum and the prosthesis base surfaces, which are introduced by the user in the graphical display using the digital wax knife, are transferred into the digital prosthesis model by the data-processing device.

In a preferred embodiment of the system, the data-processing device is adapted to provide a multiplicity of predetermined surface textures for selection, and to make these applicable after selection by the user to regions of the surfaces of the digital prosthesis model which have been selected by the user, and transfer them into the digital prosthesis model.

In a preferred embodiment of the system, the data-processing device is adapted to call up at least one gingiva parameter for specification, to which at least one of the following parameters belongs: gingival frame of the tooth lengths of the installed teeth, minimum wall thickness of upper and lower jaw bases, surface texture parameters of the palate surface and geometrical parameters of the transition region from the prosthesis base body to the tooth, the data-processing device being adapted to transfer entered gingiva parameters into the digital prosthesis model.

In a preferred embodiment of the system, the data-processing device is adapted to call up at least one tooth cavity parameter for specification by the user, the width of the adhesive gap between the inner wall of the tooth cavity and the inserted tooth base and the position and number of spacers on the inner wall of the tooth cavity for defined positioning of the base of the inserted tooth with a uniformly wide adhesive gap belonging to the tooth cavity parameters, and to transfer the specified tooth cavity parameters for all tooth cavities into the digital prosthesis model.

In a preferred embodiment of the system, the data-processing device is adapted, during the calculation of the cavities for prefabricated plastic teeth, to establish whether the remaining wall thickness of the prosthesis base below the cavity would fall below a predetermined minimum wall thickness, and if so to store the length to which the plastic tooth is to be reduced in order to comply with the predetermined minimum wall thickness below the cavity, to adapt the cavity to the reduced length of the plastic tooth and to store it in the digital prosthesis model. Subsequently, the data-processing device may control a milling device with these data in such a way that the prefabricated plastic tooth is shortened to the stored reduced length of the plastic tooth.

In a preferred embodiment of the system, the data-processing device is furthermore adapted to provide a selection menu for artificial teeth made of different materials, in which a material selection from dental material is possible for each tooth position, the data-processing device furthermore being adapted to take the selected material type into account during the calculation of the cavities in the prosthesis base bodies.

In a preferred embodiment of the system, the bite fork has an inner bite arch and an outer arch, which is applied thereon using articulations and is to be aligned parallel to the Camper plane and parallel to the bipupillar line, whereupon the resulting deviation of the parallelism of the inner bite arch relative to the aligned outer arch can be read from scales on the articulations.

The invention will be described below with the aid of an exemplary embodiment in the figures, in which.

The production of a dental prosthesis using a method and system according to the invention, in which individualized impression trays are used, will first be explained below.

Figure 1:
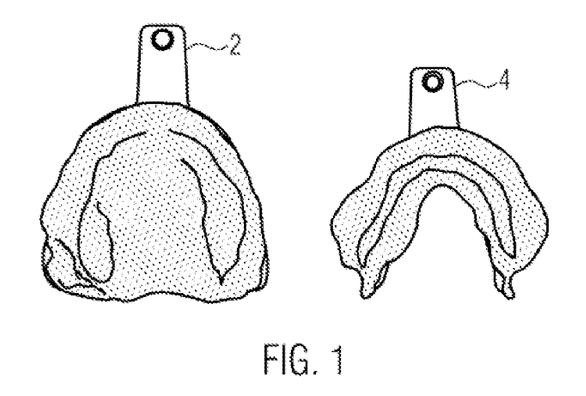
FIG. 1 shows a plan view of standard impression trays for upper and lower jaw bases, with plastic material therein.
Figure 2:
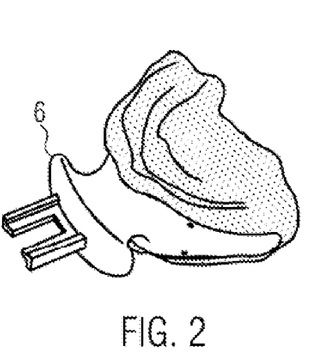
FIG. 2 shows a perspective view of a centric tray for position determination of the upper jaw and lower jaw.

FIG. 1 shows a plan view of standard impression trays 2, 4, with which the shapes of the upper and lower jaw bases have been taken with plastic material contained therein. FIG. 2 shows the way in which a first position determination of the upper jaw with respect to the lower jaw has been carried out with a centric tray 6 (device for determining the intervestibular relation).

Figure 3:
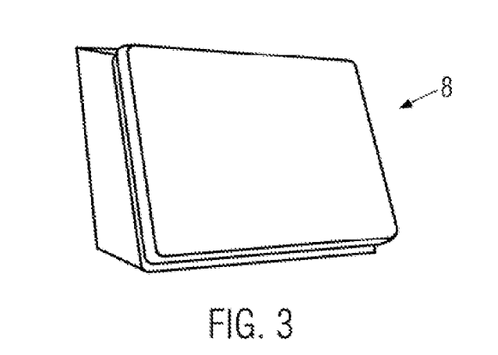
FIG. 3 shows a sampling device for scanning the impressed shapes of the upper and lower jaw bases.

These shapes of the upper and lower jaw bases which have been taken are scanned in a sampling apparatus 8 represented in FIG. 3 and are stored in digitized form in the data-processing device.

Figure 4:
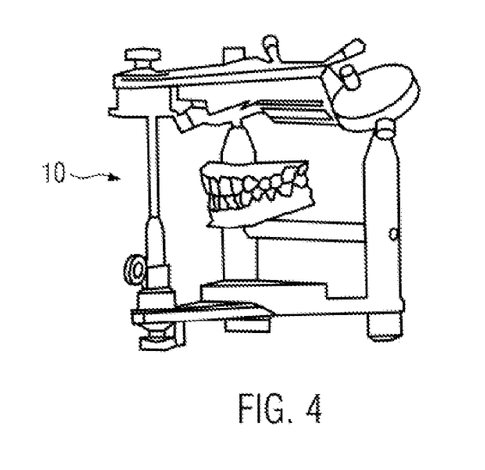
FIG. 4 shows the shapes of the upper and lower jaw bases in a virtual articulator.

FIG. 4 schematically represents the way in which the shapes of the upper and lower jaw bases are positioned in a virtual articulator in the data-processing device by means of the position determination carried out, that is to say the chewing movements are simulated in the virtual articulator after the positioning with the digital prosthesis model.

Figure 5:
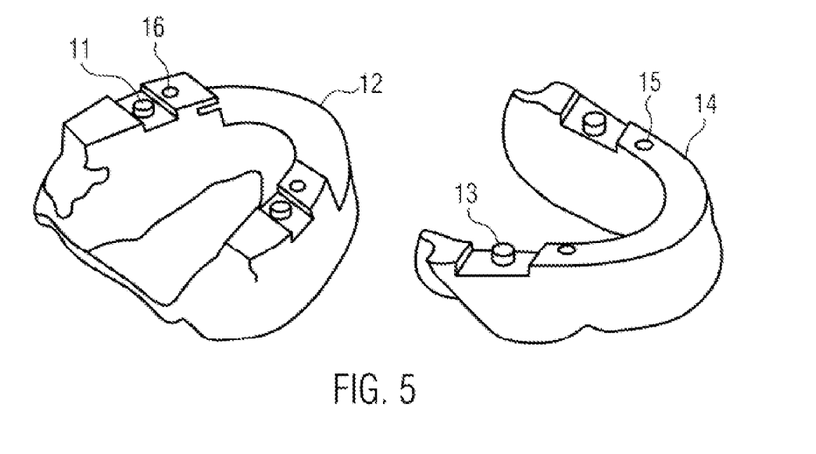
FIG. 5 shows perspective views of the individualized impression trays produced on the basis of the scanned data of the shapes taken of the upper and lower jaw bases.
Figure 6:
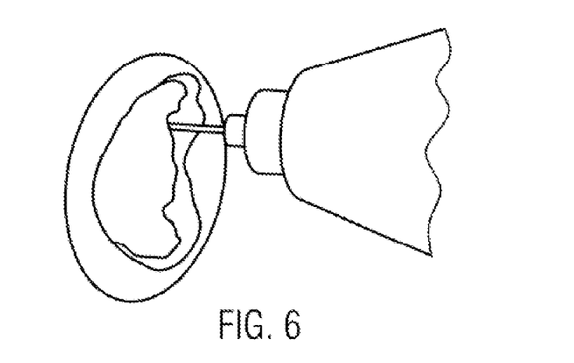
FIG. 6 shows a perspective view of an individualized impression tray during its production in a CAD/CAM-controlled machine on the basis of the scanned data of the shapes of the upper and lower jaw bases.

On the basis of the digital prosthesis model thus initially obtained, in a CAD/CAM-controlled manufacturing apparatus, as represented in FIG. 6, the individualized impression trays 12, 14 are produced from a blank, in the present example by an ablative milling method. The individualized impression trays which are produced are represented in FIG. 5, in which produced pins 11, 13 and reception recesses 15, 16 for receiving registering elements can also be seen.

Figure 7:
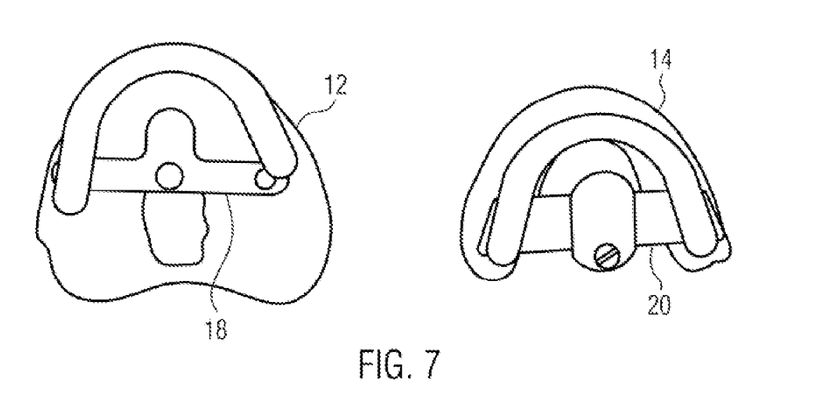
FIG. 7 shows plan views of the finished individualized impression trays.

FIG. 7 shows plan views of the individualized impression trays 12 and 14 which have been produced, with registering elements 18 and 20 fastened thereon.

Figure 8:
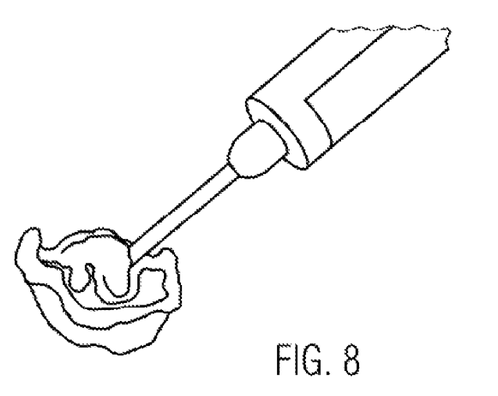
FIG. 8 shows a view of an individualized impression tray when filling with plastic material, FIGS. 9a)-c) show perspective views of a bite fork, of the bite fork when determining the occlusal plane, and a detail view of the bite fork with a scale for displaying data concerning the position of the occlusal plane.
Figure 9A:
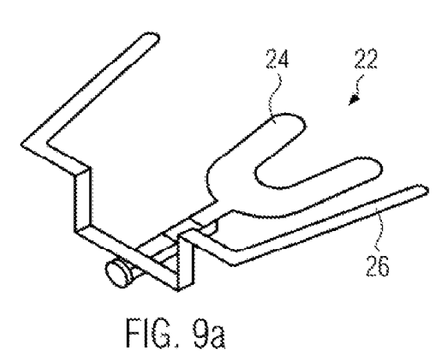
Figure 9B:
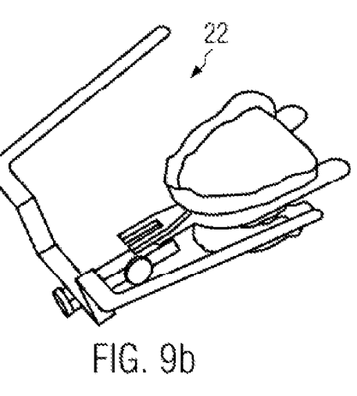
Figure 9C:
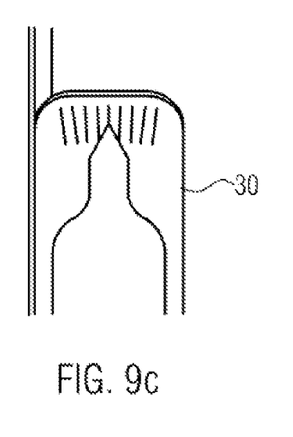

FIG. 8 shows the way in which an individualized impression tray is filled with plastic material. The detailed shapes of the upper and lower jaw bases are taken with the individualized impression trays 12, 14 and plastic material located thereon. The functional movements of the patient are to be carried out during the impression. The position of the occlusal plane is also determined in this case, to which end a bite fork as represented in FIG. 9a is used. The bite fork 22 has an inner bite arch 24, which is introduced between the individualized impression trays 12, 14 during the impression process just mentioned. The inner bite arch 24 is connected to an outer arch 26 via articulations, which, with a rigidly located inner bite arch 24, make it possible to bring the outer arch 26 parallel to the Camper plane and align the outer arch 26 parallel to the bipupillar line. This involves a relative movement of the outer arch 26 with respect to the rigidly located bite arch 22, which is made possible by the articulations. The relative position of the inner bite arch 24 when the outer arch 26 is aligned can then be measured with the aid of the adjustment of the articulations, to which end each articulation is provided with a scale 30 which shows the adjustment which has been carried out and therefore indicates the position parameters of the inner bite arch 24 relative to the outer arch 26 aligned with the Camper plane and parallel to the bipupillar line. The position parameters which have been read are stored as parameters of the occlusal plane.

Figure 10:
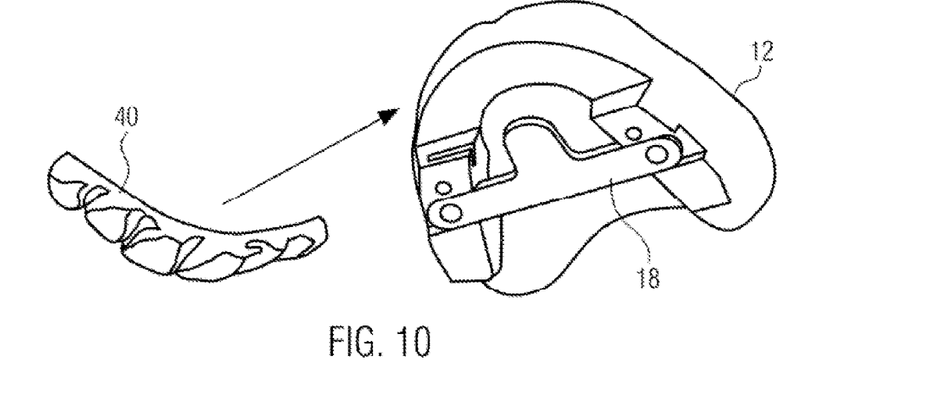
FIG. 10 shows a perspective view of an individualized impression tray for the upper jaw during the addition of a selected standard front dental arch.

FIG. 10 schematically represents the way in which, during the impression, i.e. while the individualized impression trays 12, 14 are located in the patient's mouth, a standard front dental arch 40 matching the patient is selected from a provided set of upper or lower standard front dental arches. As a function of the physiological situation, the selected standard front dental arch 40 is positioned on the associated individualized impression tray 12 according to the relevant physiological situation and fastened on the impression tray 12 by a fastening means. The fastening means may for example be a wax block, photocuring material which is cured after final positioning, or an adjustable mechanism which is fitted on the individualized impression tray in a recess provided therefor. In this example, the standard front dental arch contains six adjacent front teeth; in principle, standard front dental arches with a different number of front teeth may also be used.

The set of standard front dental arches may, for example, contain front dental arches with different front tooth sizes (small/medium/large) and different front dental arch sizes (wide/medium/narrow). Each standard front dental arch may, for example, comprise six front teeth.

Figure 11:
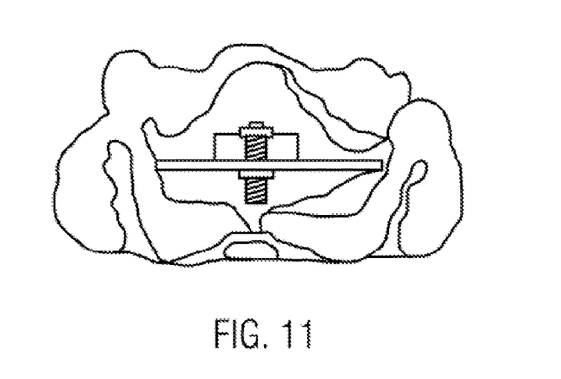
FIG. 11 shows a view of the individualized impression trays after the jaw relation determination by means of an incisal pin record.

FIG. 11 represents the way in which, during the jaw relation determination by means of an incisal pin record, the exact vertical and horizontal position of the upper jaw with respect to the lower jaw is determined. This position of the two individualized impression trays is fixed by a suitable material in the patient's mouth. The two connected impression trays, with the shapes of the upper and lower jaw bases taken in the plastic material held therein and with a standard front dental arch fastened on one of the impression trays, are introduced in a connected, registered bite position into a sampling device 8, for example as shown in FIG. 3, in order to provide a starting point for the digital prosthesis model by sampling the shape and digitized storage thereof. The digitized shapes of the upper and lower jaw bases are positioned with an average value in the determined jaw relation in the virtual articulator in the data-processing device, as shown in FIG. 10.

If deviations from the zero position of the scales were registered during the position determination of the occlusal plane, the deviating values are to be entered into the data-processing device. The position of the occlusal plane is adapted according to the specifications.

Figure 12:
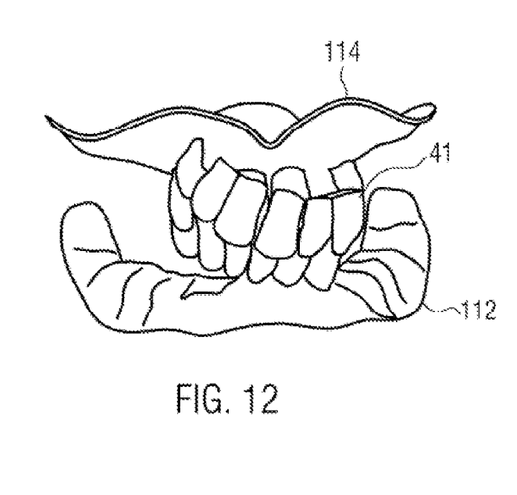
FIG. 12 shows a representation of the digital prosthesis model during integration of the standard front dental arch shape data, called up from a database, of the selected standard front dental arch.

The further construction and refinement of the digital prosthesis model then takes place in the data-processing device, which delivers a display of the spatial digital prosthesis model, as schematically shown in FIG. 12.

For the physically selected standard front dental arch, the identification of which is entered into the data-processing device, a data set of digital standard front dental arch shape data for the selected standard front dental arch is then called up by the data-processing device from a database. This digital model of the selected standard front dental arch is then integrated into the digital prosthesis model in such a way that the position of the digital model of standard front dental arch shape data which has been called up relative to the digitized jaw base data matches as well as possible the position of the scanned data of the standard front dental arch fastened on the impression tray in the digital prosthesis model. This is indicated in FIG. 12 by showing the digital model 41 of the selected standard front dental arch relative to the digitized upper jaw base 114 in different positions, these positions being varied until the best possible correspondence for the scanned data of the physical standard front dental arch 40 with respect to the upper jaw base is achieved. As soon as the optimal positioning of the digital model of the selected standard front dental arch is achieved, this digital model 41 of the selected standard front dental arch is integrated into the digital prosthesis model in the correct relative position with respect to the upper jaw base 114.

Figure 13:
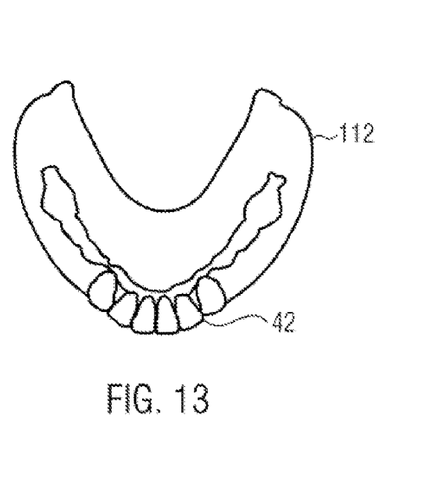
FIG. 13 shows a representation of the digital prosthesis model of the lower jaw base from above.

The data-processing device is then furthermore adapted to call up an antagonist standard front dental arch, which matches the selected standard front dental arch, from the database of the digital models for the standard front dental arches. If a plurality of antagonist front dental arches in the database are declared potentially suitable for the selected standard front dental arch, these are shown for selection by the data-processing device. Subsequently, the digital model data of the selected antagonist standard front dental arch 42 are combined with the digitized data of the digital prosthesis model of the associated jaw base, in such a way that an optimal setting/position with the already previously selected digital data of the selected standard front dental arch 41, which have been integrated into the digital prosthesis model, is achieved. This is represented in FIG. 13, where a matching antagonist standard front dental arch has been integrated into the lower jaw of the digital prosthesis model after the positioning of the digital model of the selected standard front dental arch 41 for the upper jaw has already taken place in FIG. 12.

Figure 14:
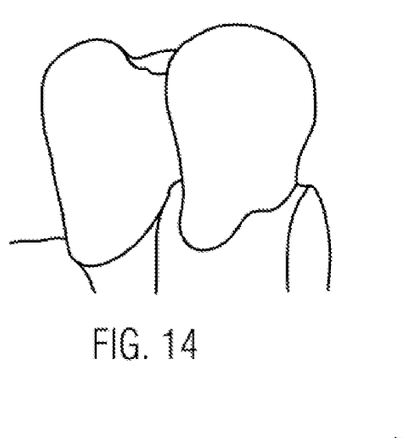
FIG. 14 shows a perspective detail view of the digital prosthesis model during integration of premolar tooth rows, called up from the database, into the digital prosthesis model.
Figure 15:
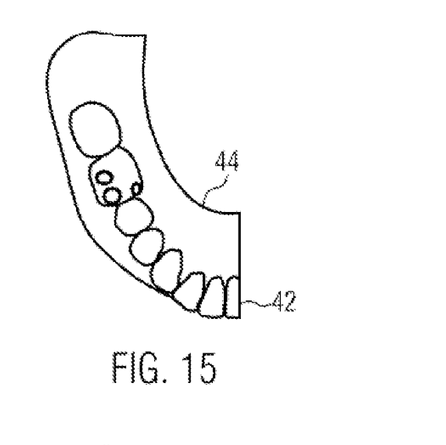
FIG. 15 shows a plan view of the lower jaw of the digital prosthesis model during the insertion of premolar tooth rows.
Figure 16:
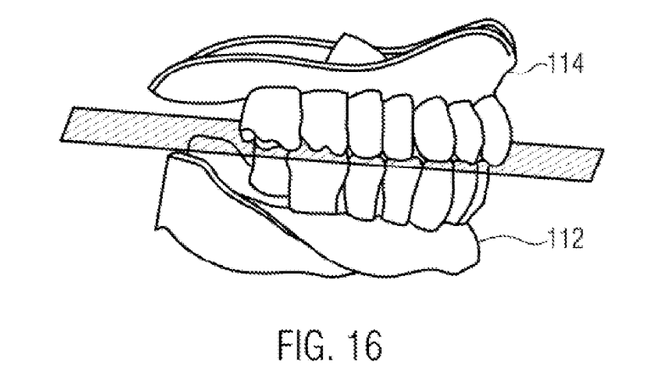
FIG. 16 shows a perspective representation of the digital prosthesis model with integrated tooth shape data of all teeth during the functional check of the positioning with a digital articulator.

FIG. 15 shows a schematic plan view from above of the lower jaw base 112 of the digital prosthesis. The digital standard front dental arch shape data 42 are already integrated therein. The data-processing device is now adapted to call up, from the database, one or more, if there are several, premolar tooth rows 44 declared as matching the already integrated standard front dental arch in the database. When there are a plurality of possible premolar tooth rows, these are offered by the data-processing device to the user for selection. After selection, the digital model data of the selected premolar tooth row are called up from the database and entered into the jaw base data of the digital prosthesis, while taking into account the occlusal plane, the position of which has already been determined. FIG. 14 shows a lateral point of contact of the premolar tooth row with the front dental arch, only the last tooth lying at the contact point from the premolar tooth row and the front dental arch being shown in each case.

Thus, the tooth data of all teeth are successively entered in their position into the digital prosthesis. A functional check of the positioning is carried out with the digital articulator. The data-processing device is in this case adapted to detect and store functional contact defects in the occlusion and in the occlusion movement. Contact defects can subsequently be removed by the user using grinding technology.

Figure 17:
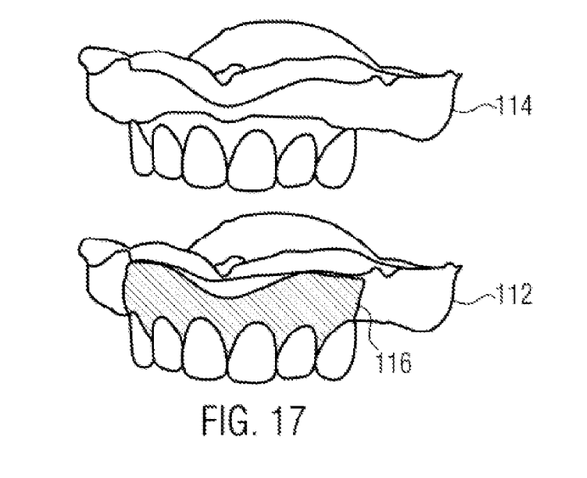
FIG. 17 shows perspective representations of the digital prosthesis model during the modelling of the gum by means of a digital wax knife.

As shown in FIG. 17, a graphical representation of the digital prosthesis model is shown by the data-processing device in accordance with the specifications of the jaw base data and the tooth installation, as represented in FIG. 17, top. The data-processing device furthermore provides a so-called "digital wax knife" as a program function. With this, a user can configure the shape of the gum in the graphical representation by the digital wax knife generating the desired configuration in the graphical representation. The desired configuration of the gum 116 is shown in the lower representation in FIG. 17. The gum configuration generated in this way by the user is transferred into the digital prosthesis model.

Furthermore, a multiplicity of predetermined surface textures are provided by the data-processing device for selection, which the user can select and apply to selected regions of the surfaces of the digital prosthesis model, after which they are transferred into the digital prosthesis model.

For further configuration of the gingiva, a number of gingiva parameters are offered by the data-processing device to the user for specification. These include:

1. gingival frame of the tooth lengths of the installed teeth, i.e. the depth of the cavity which receives the tooth base in the jaw base,
2. minimum wall thickness of upper and lower jaw bases, i.e. the minimum thickness of the wall thickness of the base remaining below a cavity,
3. surface texture parameters of the palate surface, and
4. geometrical parameters of the transition region from the prosthesis base body to the tooth in the cavity. With the latter geometrical parameters, the user can configure the transition region from the prosthesis base surface to a cavity, and may for example provide rounding.

By rounding or chamfering on the upper edge, the cavity is widened slightly on the upper edge. This creates a slightly widened edge around the tooth base in the transition region to the prosthesis base surface, this widened transition region being filled with adhesive when adhesive bonding of the artificial teeth. When antibacterial additives are used in the adhesives, improved protection against ingress or establishment of bacteria in the transition region of the tooth base and tooth cavity of the prosthesis base can thus be ensured.

It is necessary to take into account and comply with a minimum wall thickness of the upper and lower jaw bases in the region of the cavities in order to ensure a minimum strength of the prosthesis base body in the region of the cavities as well.

Figure 18:
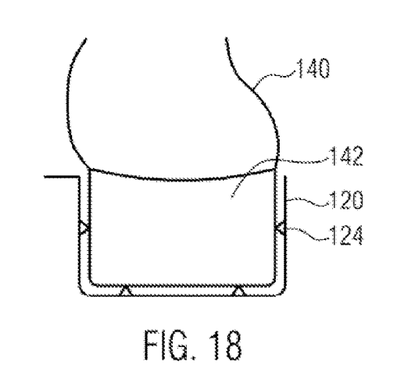
FIG. 18 shows a cross-sectional view of the digital prosthesis model in the region of a tooth cavity of the lower jaw base.

Furthermore, tooth cavity parameters are called up by the data-processing device for specification by the user. These include positioning, number and size of spacers 124 in a cavity 120, as shown in FIG. 18. These spacers 124 on the inner walls of the cavity 120 ensure that the tooth base 142 of an artificial tooth 140 inserted into the cavity 120 is held reliably positioned in the cavity 120, while simultaneously a defined intermediate space remains between the outer surface of the tooth base 142 and the inner wall of the cavity 120, so that a defined intermediate space for receiving adhesive is provided. In this way, a uniformly wide adhesive gap around the tooth base 142 in the cavity 120 is obtained when positioning the artificial tooth in the cavity of the prosthesis base. In principle, the width of the adhesive strip may also belong to the tooth cavity parameters to be specified. The specified tooth cavity parameters are then transferred for all tooth cavities into the digital prosthesis model.

Figure 20:
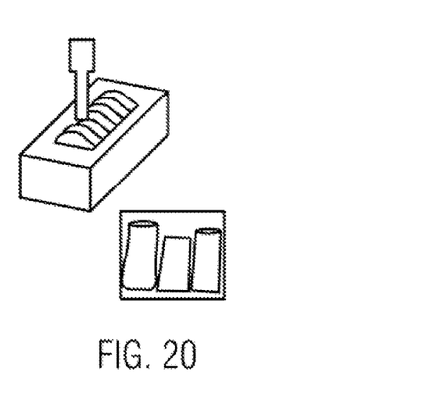
FIG. 20 shows a schematic view of prefabricated plastic teeth during the automatically controlled basal adaptation/shortening.

When, during the calculation of the cavities, it is established in the data-processing device that the remaining wall thickness of the prosthesis base below the cavity would fall below the predetermined minimum wall thickness, for the artificial tooth provided for said cavity the data-processing device stores a shortened length such that the predetermined minimum wall thickness below the cavity is maintained. In the case of using prefabricated plastic teeth, the prefabricated plastic tooth length to be shortened is then used to control an automatic milling apparatus, into which the prefabricated plastic tooth is inserted and is shortened to the shortened length. This process is schematically shown in FIG. 20.

Figure 19:
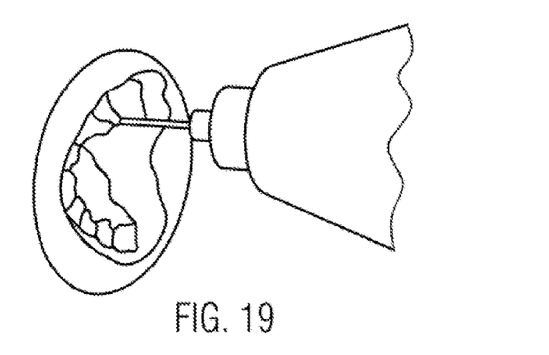
FIG. 19 shows a perspective view of a jaw prosthesis base being manufactured with a CAD/CAM manufacturing apparatus controlled on the basis of the digital prosthesis model.

After all the data and parameters in the digital prosthesis model have been specified and established, the data-processing device controls a CAD/CAM-controlled manufacturing machine in accordance with this digital prosthesis model, for example a milling machine in which the designed prosthesis base body is produced from a block consisting of gum-coloured plastic material by an ablative method, the processing of the prosthesis base body with an automatically controlled miller being shown in FIG. 19. As an alternative, the manufacture of the prosthesis base bodies may also be carried out by a constructive method.

Figure 21:
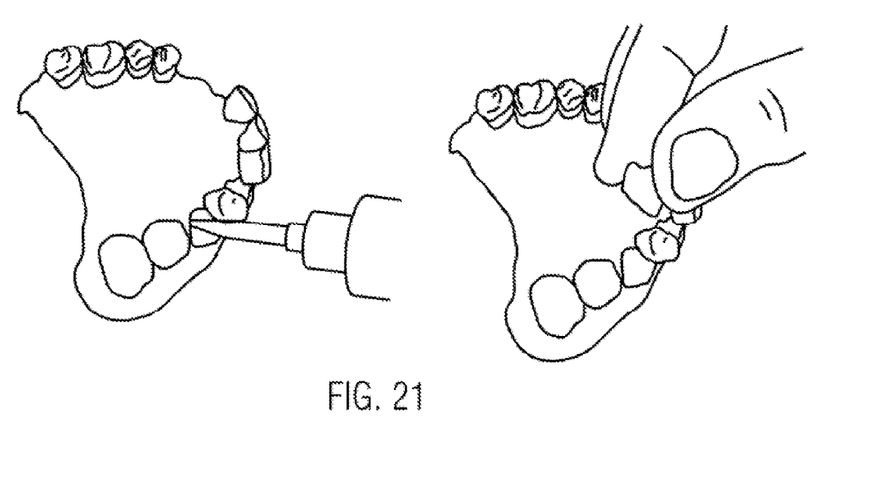
FIG. 21 shows perspective views during the insertion of prosthetic teeth into the prosthesis base.

Subsequently, the prosthetic teeth are adhesively bonded into the cavities of the manufactured prosthesis base bodies by means of a joining medium, as shown in FIG. 21.

In order to adhesively bond the artificial teeth permanently in the cavities, correct positioning is necessary. In this case, each tooth or each tooth group is to be checked individually and manually onto the correct recess in the cavity and subsequently adhesively bonded. As the checking instrument, a transfer template is to be used, which may additionally be used as a transfer instrument when adhesively bonding the individual teeth and/or tooth row. This transfer template is a negative mould of the tooth group, produced by a CAD/CAM manufacturing machine. Reliable and correct positioning is thus ensured. The teeth and/or tooth groups are positioned in the template and transferred into the cavities of the prosthesis base body during the adhesive bonding. The final polishing is carried out conventionally on a polishing unit. The prosthesis base bodies must be smooth and free of burrs, and the prosthesis edges are to be processed round and never with sharp edges.

Figure 22:
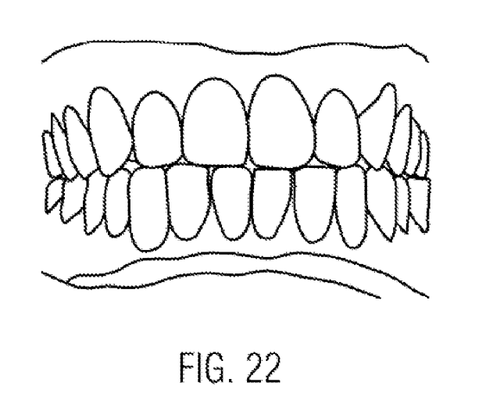
FIG. 22 shows a perspective view of the inserted dental prosthesis during the functional and aesthetic check.

FIG. 22 illustrates the functional and aesthetic check of the manufactured partial prosthesis in the patient's mouth.

Figure 32:
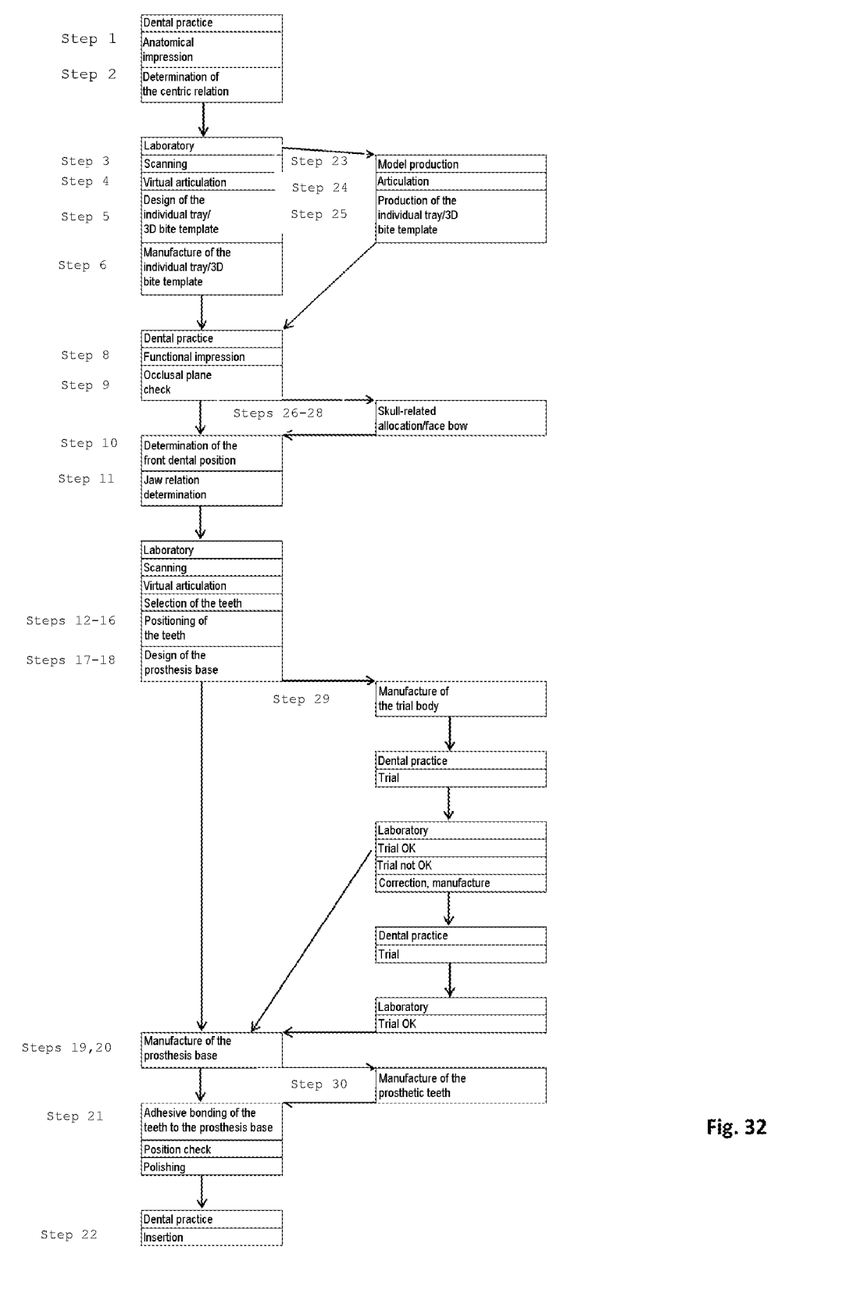
FIG. 32 shows a flow diagram including the steps which are performed when using the system according to the invention.

FIG. 32 shows a flow chart with steps which may be employed when using the system according to the invention. In the left-hand branch, the steps according to the procedure described so far with the aid of FIGS. 1 to 22 are carried out, numbers which correspond to the numbers of FIGS. 1 to 22 illustrating these steps in the preceding description of the figures being indicated on the blocks of the process steps. The steps 23 to 30 listed in the right-hand branches are optionally additional or alternatively possible steps within the process, which may be carried out on the process steps represented. These steps 23 to 30 will be described below with the aid of FIGS. 23 to 30 illustrating these steps.

Figure 23:
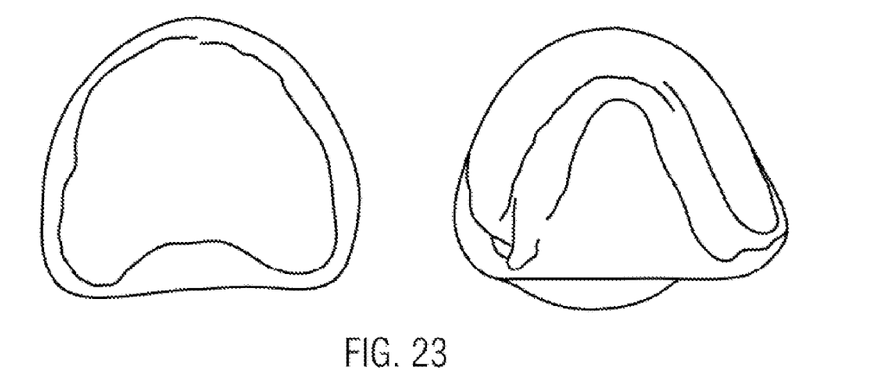
FIG. 23 shows a plan view of situation models of the upper and lower jaw bases, produced with dental putty gypsum.

FIG. 23 shows the situation models which are produced. Production is carried out in a standard way with class 3 dental gypsum.

Figure 24:
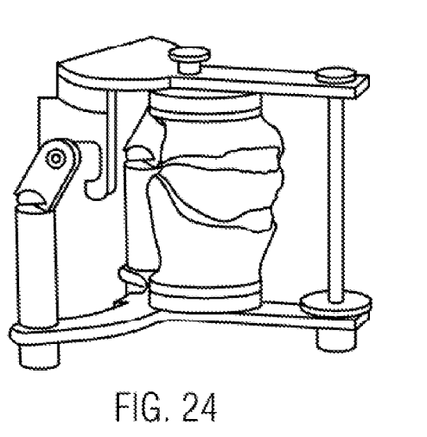
FIG. 24 shows a perspective representation of the models of upper and lower jaw bases inserted into an articulator.

As shown in FIG. 24, the models of the upper and lower jaw bases are placed with an average value in the articulator.

Positioning of upper jaw and lower jaw is possible with the position determination carried out by means of a centric tray.

Figure 25:
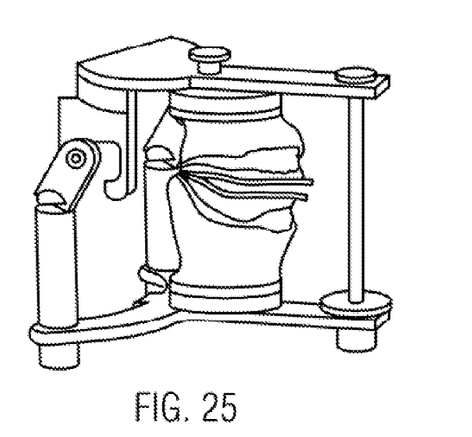
FIG. 25 shows a perspective view of the models in the articulator after production of individualized impression trays.

As shown in FIG. 25, an individualized impression tray is produced from photocuring or autopolymerizing tray material on the basis of the information obtained in this way. The registering elements are directly polymerized in during this.

Figure 26:
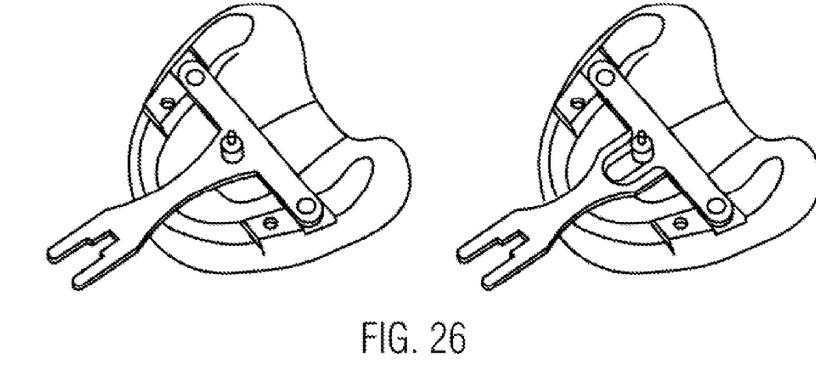
FIG. 26 shows perspective views of the individualized impression trays which have been produced, with an interface for receiving the transfer bow system.

As shown in FIG. 26, a holder/interface for the registering articulation to the skull/articulation-related allocation of the upper and lower jaw bases is provided on the registering element 18 of the individualized impression tray 12. As an alternative, the registering element itself may be replaced.

Figure 27:
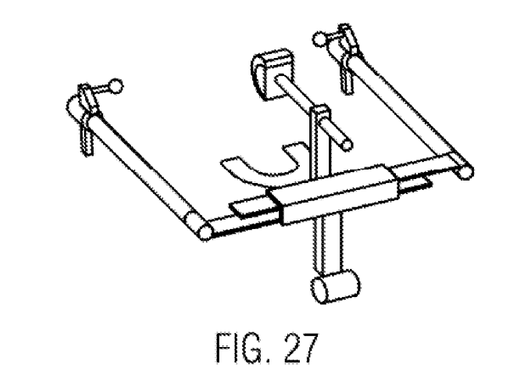
FIG. 27 shows a perspective view of a transfer bow system for alignment on the patient.
Figure 28:
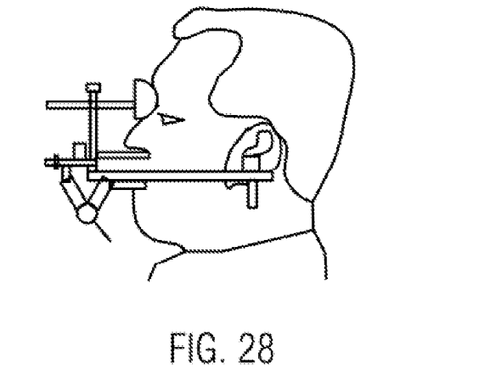
FIG. 28 shows a perspective view of the transfer bow system positioned on the patient.

FIG. 27 shows a transfer bow system. When the transfer bow system is aligned on the patient, the adjustment screws on the registering articulation are fixed. FIG. 28 shows the situation during adjustment on the patient.

The individual position of the registering articulation is digitized by scanning. The placement position of the patient's upper and lower jaw bases can be reproduced individually in the virtual articulator.

Figure 29:
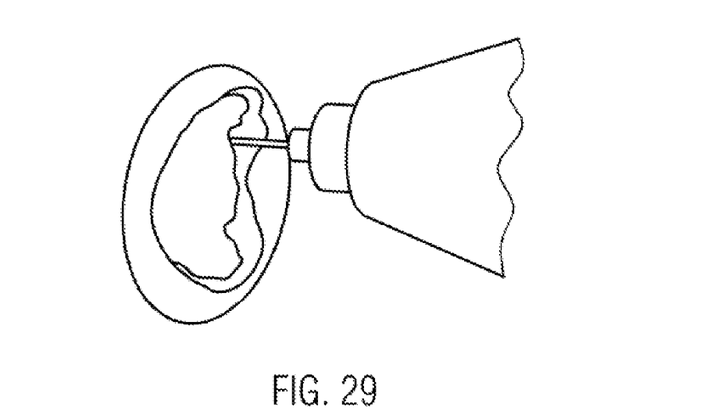
FIG. 29 shows a perspective view during the production of the designed trial body from a block in a CAD/CAM-controlled manufacturing apparatus.

FIG. 29 represents the way in which the designed trial body is manufactured by the ablative method from a block in a CAD/CAM-controlled manufacturing machine. The prosthetic teeth are subsequently provisionally adhesively bonded in the cavities.

As an alternative, the entire trial prosthesis (prosthesis base body including prosthetic teeth) may be manufactured in one piece.

The functional and aesthetic check of the trial prosthesis is carried out in the patient's mouth.

After the trial, optionally correction of the tooth position/placement and optionally new digitization in the sampling device and storage of the modified situation in the data-processing device are carried out.

After the correction, the permanent dental prosthesis or a further trial body may be manufactured.

Figure 30:
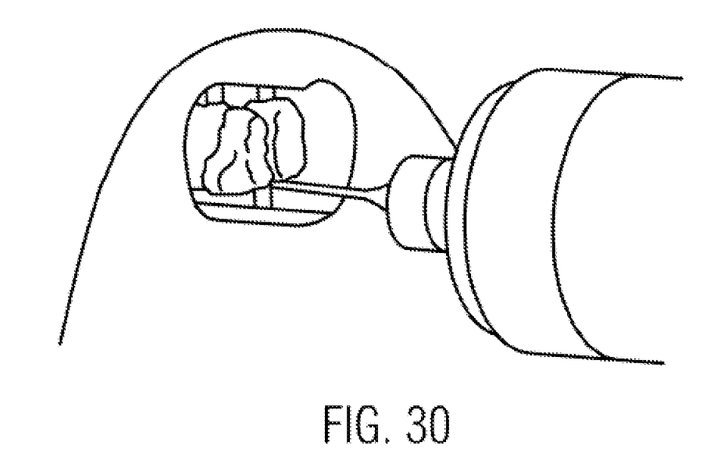
FIG. 30 shows a perspective representation of the CAD/CAM-controlled manufacturing apparatus during the manufacture of the prosthetic teeth on the basis of the data from the digital prosthesis model.
Figure 31:
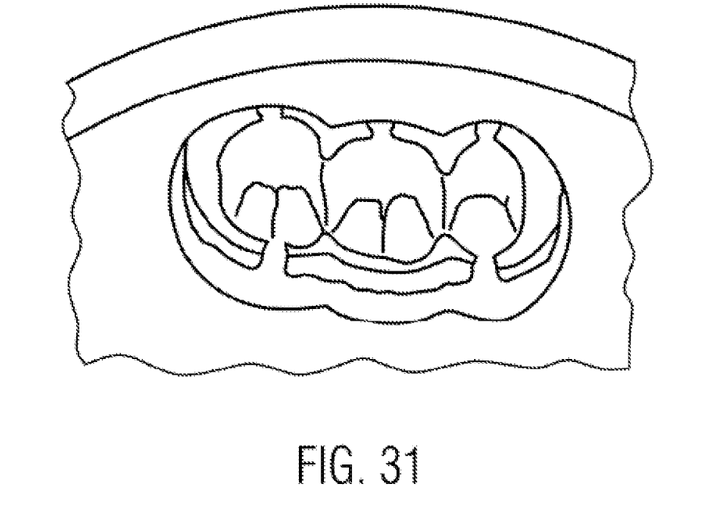
FIG. 31 shows a perspective representation of the prosthetic teeth machined from a block.

In a CAD/CAM manufacturing machine controlled by the data-processing device, the artificial teeth are manufactured in accordance with the digital prosthesis model by ablative or constructive methods, an ablative method being illustrated in FIG. 30. The prosthetic teeth machined from a block, and still connected to the block via supporting webs, are represented in FIG. 31.

The gingiva parameters defined in the data-processing device are taken into account automatically during the manufacture of the prosthetic teeth. Retrospective reduction of the tooth lengths is not necessary in this method.

LIST OF REFERENCES

2, 4 standard impression tray
6 centric tray
8 sampling device
10 virtual articulator
12, 14 individualized impression tray
11, 13 pin for attaching registering elements
15, 16 holders for inserting registering elements
18, 20 registering elements
22 bite fork
24 inner bite arch
26 outer arch
28 articulations of the bite fork
30 scale of the bite fork
40 standard front dental arch
41 digital standard front dental arch shape data
42 digital antagonist standard front dental arch shape data
44 digital premolar tooth row shape data
112 lower jaw base in the digital prosthesis model
114 upper jaw base in the digital prosthesis model
116 gum in the digital prosthesis model
120 cavity
124 spacer
140 artificial tooth
142 tooth base

The invention claimed is:

1. A method for construction of a total dental prosthesis comprising
   selecting a standard front dental arch from a set of standard front dental arches,
   inserting the standard front dental arch into an impression tray,
   taking a manual impression of upper and/or lower jaw bases using the impression tray with the dental arch inserted into the impression tray to provide a manual impression of upper and/or lower jaw bases and reference point for a set-up for a digital prosthesis model,
   scanning and storing the manual impression of the upper and/or lower jaw bases and reference-point data into a database,
   selecting standard dental teeth shape data from the database,
   integrating the selected standard dental teeth shape data into the stored reference-point data to provide a digital prosthesis model.

2. The method according to claim 1 wherein the impression tray is a standard impression tray or an individualized impression tray.

3. The method according to claim 2 wherein the individualized impression tray is manufactured from prior acquisition of data based on jaw bases using standard impressions trays or by acquiring shapes of the jaw bases by digital scanning or phototechnical acquisition.

4. The method according to claim 2, further comprising
   determining a position of an occlusal plane using a bite fork assembly having an inner bite arch and an outer arch,
   inserting and fastening the inner arch between the standard impression trays or the individualized impression trays
   adjusting the outer arch to align parallel to a Camper plane and parallel to a bipupillar line,
   inputting the occlusal plane data received from bite fork assembly into the database, and
   integrating the occlusal plane data into the stored reference-point data.

5. The method according to claim 1 further comprising
   selecting an antagonist front dental arch for the upper or lower jaw to match the selected standard dental teeth shape data of an opposing upper or lower jaw that is already part of the prosthesis model, and
   combining the selected antagonist front dental arch data into the digital prosthesis model.

6. The method according to claim 5 further comprising
   selecting one or more premolar tooth rows matching the selected standard front dental teeth shape data, and
   entering the one or more premolar tooth rows into the digital prosthesis model.

7. The method according to claim 6, further comprising
   generating a graphical representation of the digital prosthesis model,
   providing a digital wax knife in order to allow a user to design a gum and prosthesis base surfaces with the digital wax knife in the graphical representation of the digital prosthesis model, and
   transferring the designed gum and prosthesis base surfaces to the digital prosthesis model.

8. The method according to claim 7, further comprising
   providing a multiplicity of predetermined surface textures for selection into the digital prosthesis model, and selecting and applying a surface texture to the digital prosthesis model.

9. The method according to claim 8, further comprising selecting at least one gingiva parameter from the database,
transferring the at least one gingiva parameter into the digital prosthesis model,
wherein the at least one gingiva parameter comprises one of more of gingival frame of tooth lengths of installed teeth, minimum wall thickness of upper and lower jaw bases, surface texture parameters of a palate surface and geometrical parameters of a transition region from the prosthesis body to the tooth.

10. The method according to claim 9, further comprising selecting at least one tooth cavity parameter from the database,
wherein the at least one tooth cavity parameter comprises width of an adhesive gap between an inner wall of the tooth cavity and an inserted tooth base and position and number of spacers on an inner wall of the tooth cavity for defined positioning of a base of the inserted tooth with a uniformly wide adhesive gap relative to inner surfaces of the tooth cavity, and
transferring the selected tooth cavity parameters for all tooth cavities into the digital prosthesis model.

11. The method according to claim 10, further comprising evaluating wall thickness of the prosthesis base below the tooth cavity parameter to determine if the wall thickness is below a predetermined minimum wall thickness, and
reducing length of teeth to be placed in tooth cavity in order to obtain a predetermined minimum wall thickness below the cavity.

12. The method according to claim 11, further comprising providing a selection menu for artificial teeth made of different material types, in which a material selection from dental materials is possible for each tooth position, the selected material type being taken into account in the database during calculation of cavities in the prosthesis bases.

13. The method according to claim 1, further comprising producing the dental prosthesis from the digital prosthesis model by ablative or constructive methods.

* * * * *